United States Patent [19]

Gattaz

[11] Patent Number: 5,006,462

[45] Date of Patent: Apr. 9, 1991

[54] METHOD FOR THE DETECTION OF SCHIZOPHRENIA

[75] Inventor: Wagner F. Gattaz, Heidelberg, Fed. Rep. of Germany

[73] Assignee: Abbott Laboratories, Abbott Park, Ill.

[21] Appl. No.: 168,709

[22] Filed: Mar. 16, 1988

[51] Int. Cl.$^5$ .......................... G01N 33/53; C12Q 1/44
[52] U.S. Cl. .......................................... 435/7.4; 435/4; 435/19; 436/501; 436/518; 560/121; 424/88
[58] Field of Search ................. 435/4, 7, 19; 436/501, 436/518; 560/121; 424/88

[56] References Cited

U.S. PATENT DOCUMENTS 4,302,447  11/1981  Horrobin ........................ 424/643 X

OTHER PUBLICATIONS

Biological Abstract 84(1)9273: Gattaz et al., "Increased Plasma Phospholipase A2 in Schizophrenic Patients...", *Biol. Psychiatry* 22(4): 421–426, 1987.

Smith et al., Principles of Biochemistry, 7th ed., (McGraw-Hill Book Company), pp. 551–552 (1983).

Thuren et al., "Fluorometric Assay for Phospholipase A2 in Serum", Clin. Chem. 31(5): 714–717 (1985).

*Primary Examiner*—Esther L. Kepplinger
*Assistant Examiner*—Carol A. Spiegel
*Attorney, Agent, or Firm*—Daniel R. Curry

[57] ABSTRACT

The diagnosis of schizophrenia through the detection of a phospholipase enzyme is disclosed. In this invention, a test sample from the patient can be combined with a test composition to measure phospholipase enzyme in the test sample. The sample can be read and the result compared with a scale of values found in nonschizophrenic controls.

28 Claims, 2 Drawing Sheets

METHOD FOR THE DETECTION OF SCHIZOPHRENIA

TECHNICAL FIELD

This invention relates to a method for the diagnosis of schizophrenia. In particular it relates to the determination of phospholipase-A2 activity or concentration in biological fluids for the diagnosis of schizophrenia.

BACKGROUND INFORMATION

Studies of different neurodiagnostic subgroups indicate the presence of brain dysfunction in at least some schizophrenic patients. These studies have been summarized in reviews that suggest that the brain dysfunction in schizophrenia could occur as the result of a faulty maturation of the central nervous system during infancy and adolescence. Accordingly, one strategy in the biological research of schizophrenia is the investigation of variables that could play a role in the plasticity of the brain.

Phospholipase-A2 (hereinafter "PLA2") is a key enzyme in the metabolism of phospholipids, catalyzing the release of fatty acids and highly toxic compounds, such as lysophosphatidylcholine. Extracellular PLA2 is synthesized in the pancreas as a digestive enzyme, whereas intracellular PLA2 controls the phospholipid turnover in the cell membrane, in turn affecting membrane integrity and membrane function.

Whereas a role for PLA2 has been described in clinical conditions such as acute pancreatitis and pancreatic cancer, only one study of this enzyme in neuropsychiatric disorders has been reported: Gattaz et al, "Increased plasma phospholipase-A2 activity in schizophrenic patients: reduction after neuroleptic therapy", *Biological Psychiatry* 22:421-426 (1987). Because PLA2 may play an important role in neuronal plasticity and neuronal function, the activity of this enzyme in schizophrenic patients and healthy controls as well as in a small group of nonschizophrenic psychiatric patients was investigated.

SUMMARY OF THE INVENTION

The present invention encompasses the detection of PLA2, in biological samples, an increased level of which may be an etiopathologic marker of schizophrenia. Thus, the detection and quantitation of this marker in biological samples can be useful as a relatively specific method for the early diagnosis of schizophrenia.

In a preferred embodiment of this invention, a plasma sample from the patient is combined with a fluorometric assay composition to measure the level of PLA2 activity in the test sample. The sample can be read by a spectrofluorometer and the result compared with a scale of PLA2 values found in nonschizophrenic or healthy controls. The practice of this invention by direct enzyme activity assay, as well as by assays involving the use of specific binding members and other types of assay methodologies are also contemplated, as is the practice of the invention by automated or instrumental methods.

DETAILED DESCRIPTION OF THE INVENTION

Figure 1:
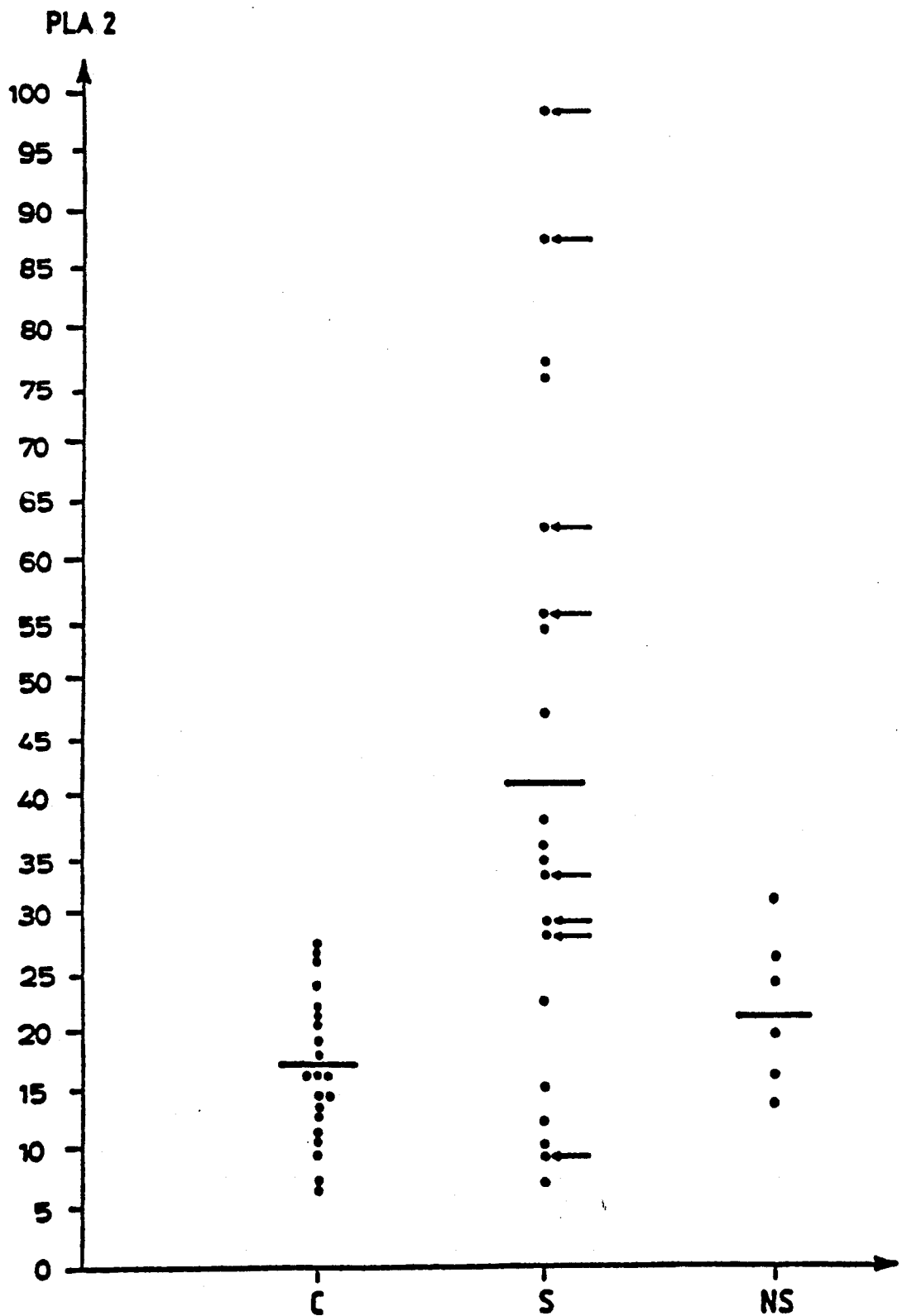
FIG. 1 is a graphical representation showing plasma PLA2 activity levels in healthy controls (C), in drug-free schizophrenics (S), and in drug-free nonschizophrenic patients (NS). The arrows indicate first-onset schizophrenic patients. (See Results: Baseline Comparisons.)

Simply stated, the method of this invention requires only three steps; combining a test sample from the patient with a PLA2 test composition, measuring the level of PLA2 in the test sample, and comparing the result with a scale of PLA2 values based on the results of healthy controls. The PLA2 test composition or assay, however, can have a wide variety of formats. As described below, the direct kinetic fluorometry of PLA2 can be determined by the hydrolysis of a pyrene-labeled enzyme substrate such as 1-octacosanyl-2-(pyren-1-yl)hexanoyl-sn-glycero-3-phosphatidyl monomethyl ester (C28-O-PHPM) from which (pyren-1-yl)hexanoic acid and a lysophospholipid derivative of C28-O-PHPM are formed. A preferred test sample is plasma for determining the level of phospholipase by direct kinetic fluorometry.

While the following examples focus on the detection of the schizophrenia marker through a direct fluorometric assay of enzyme activity via enzyme binding with a fluorescently labeled substrate, other assay formats suitable in the practice of the invention include the measurement of chemiluminescence, radioactive energy emmissions, and color development, as well as immunoassays and other assays using specific binding members for the detection of PLA2. In addition, the enzyme activity of the marker and thus the amount of marker can be measured indirectly by measuring the amount of degradation products produced from a substrate by the enzyme or by measuring the degradation rate as a function of time.

A "specific binding member", as used herein, is a member of a specific binding pair, i.e., two different molecules wherein one of the molecules through chemical or physical means specifically binds to the second molecule. Therefore, in addition to antigen and antibody specific binding pairs, other specific binding pairs include, as examples without limitation, biotin and avidin, carbohydrates and lectins, complementary nucleotide sequences, effector and receptor molecules, enzyme cofactors and enzymes, enzyme inhibitors and enzymes, and the like. Furthermore, specific binding pairs can include members that are analogs of the original specific binding member, for example an analyte-analog. If the specific binding member is an immunoreactant it can be, for example, an antibody, antigen, hapten, or complex thereof, specific for the analyte of interest, and if an antibody is used, it can be a monoclonal or polyclonal antibody, a recombinant antibody, a mixture(s) or fragment(s) thereof, as well as a mixture of an antibody and other specific binding members. In addition, the schizophrenia marker can be any substance for which there exists a naturally occurring specific binding member (e.g., an antibody) or for which a specific binding member can be prepared. Thus, it is important that the schizophrenia marker be capable of binding to at least one specific binding member in the assay configuration of choice.

Possible assay configurations well known in the art and which can benefit by the improvements contemplated by the present invention include, without limitation, sandwich and competitive assays, both solid and liquid phase, and direct and indirect, as well as forward and reverse formats for such assays.

In a liquid phase or homogenous assay, the assay reagents are all soluble and the assay reaction takes place in a liquid medium. Alternatively, the solid phase immunoassay is a commonly used immunoassay technique wherein the presence of an analyte is indicated by means of a reaction on a "solid phase" such as paper, a fiber matrix, polymeric particles or beads, or other solid material.

An example of a conventional solid phase enzyme immunoassay configuration uses an anti-analyte antibody (capture antibody) bound to an insoluble solid phase material, such as polystyrene beads or latex microparticles associated with a fibrous matrix. A second anti-analyte antibody is labeled to form a soluble indicator reagent (the second antibody can be labeled with a radioisotope, fluorophore, chemilumiphore, enzyme, or any readily detected signal generator.) The two antibody conjugates form an insoluble ternary immunocomplex ("sandwich") with the analyte when the latter is present in the test sample. Prior to the detection or measurement of the signal, the immunocomplex is separated from excess indicator reagent and other interfering substances by physically removing the solid phase-bound immunocomplex from the reaction mixture. When measured, the amount of labeled antibody associated with the solid phase bound sandwich is directly proportional to the amount of analyte in the test sample.

An alternative methodology is the competitive assay. The capture mechanism again uses an anti-analyte antibody conjugated to the insoluble solid phase, but labeled analyte (rather than a second antibody) is used as an indicator and is simultaneously incubated with the test sample and solid phase. Therefore, in the competitive assay the indicator competes with analyte present in the sample to bind with the solid phase, and a two-component immunocomplex is formed, i.e., a solid phase/analyte conjugate and/or a solid phase/indicator conjugate. In the competitive assay, the quantity of captured indicator reagent is inversely proportional to the amount of analyte present in the sample.

The assays described above also can be referred to as "direct" assays because the specific binding members directly react with the analyte. In an "indirect" assay, the specific binding member of either or both the indicator and capture reagents can be specific for an ancillary specific binding member, which itself is specific for the analyte.

In addition, the assays can be performed as "forward/sequential" or "reverse/simultaneous". In a "forward" assay the solid phase capture reagent is contacted to the sample to capture the analyte and is then washed to remove the residue of the sample prior to contact and incubation with the indicator reagent. The "reverse" assay uses a simultaneous or single incubation step wherein the capture reagent and indicator reagent are contacted to the sample at the same time.

An example of a direct specific binding assay for the phospholipase enzyme can use a first phospholipase antibody that is bound to a solid phase to capture active phospholipase and a second labeled antibody specific for phospholipase to detect and quantitate the enzyme.

Definitions (a) INDICATOR REAGENT

The indicator reagent comprises a label conjugated to a specific binding member. The indicator reagent produces a detectable signal at a level relative to the amount of an analyte in the test sample. In general, the indicator reagent is detected or measured after it is captured on the solid phase material, but the unbound indicator reagent also can be measured to determine the result of an assay.

In addition to being either an antigen or an antibody member of a specific binding pair, the specific binding member of the indicator reagent can be a member of any specific binding pair including either biotin or avidin, a carbohydrate or a lectin, a complementary nucleotide sequence, an effector or a receptor molecule, an enzyme cofactor or an enzyme, an enzyme inhibitor or an enzyme, or the like. An immunoreactive specific binding member can be an antibody, antigen, or antibody/antigen complex that is capable of binding either to the analyte as in a sandwich assay, to the capture reagent as in a competitive assay, or to an ancillary specific binding member as in an indirect assay. If an antibody is used, it can be a monoclonal antibody, polyclonal antibody, antibody fragment, recombinant antibody, a mixture thereof, or a mixture of an antibody and other specific binding members. The details of the preparation of such antibodies and their suitability for use as specific binding members are well known and will not be repeated here.

The label of the indicator reagent is capable of producing a measurable signal detectable by external means. The various labels can include chromogens, catalysts, fluorescent compounds, chemiluminescent compounds, radioactive labels, and direct visual labels. The selection of a particular label is not critical, but it will be capable of producing a signal either by itself or in conjunction with one or more additional substances. A variety of different indicator reagents can be formed by varying either the label or the specific binding member.

(b) CAPTURE REAGENT

The capture reagent of the present invention is a specific binding member, specific either for the analyte as in a sandwich assay, for the indicator reagent and analyte as in a competitive assay, or for an ancillary specific binding member, which itself is specific for the analyte, as in an indirect assay.

The specific binding member of the capture reagent can be any molecule capable of specifically binding with another, just as in the indicator reagent specific binding members. The specific binding member of the capture reagent can be an immunoreactive component such as an antibody, antigen, or antibody/antigen complex. If an antibody is used, it can be a monoclonal antibody, polyclonal antibody, antibody fragment, recombinant antibody, a mixture thereof, or a mixture of an antibody and other specific binding members.

(c) SOLID PHASE MATERIAL

The present invention also can include a solid phase material. In a homogenous system, once complex formation occurs, the solid phase can be used as a separation mechanism: the homogeneous reaction mixture is contacted with the solid phase material, and the newly formed complex(es) are retained on the solid phase material. Alternatively, the capture reagent can be retained by the solid phase material, and the reaction complex is produced in a heterogenous environment.

An assay device for the present invention can have many configurations, several of which are dependent upon the material chosen as the solid phase material. The solid phase material can include any suitable porous material. By "porous" is meant that the material is one through which fluids can flow and can easily pass. In the present invention, the solid phase material can include a fiberglass, cellulose, or nylon pad for use in a pour and flow-through assay device having one or more layers containing one or more of the assay reagents; a test strip for chromatographic techniques in which one or all of the reagents are contained in separate zones of a single strip of solid phase material; or other porous material well known to those skilled in the art. The solid phase material, however, is not limited to porous materials.

Natural, synthetic, or naturally occurring materials that are synthetically modified, can be used as a solid phase material including polysaccharides, e.g., cellulose materials such as paper and cellulose derivatives such as cellulose acetate and nitrocellulose; silica; inorganic materials such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran, and gelatin; polymeric films such as polyacrylamide; and the like. The solid phase material should have reasonable strength or strength can be provided by means of a support, and it should not interfere with the production of a detectable signal.

(d) ANCILLARY MATERIALS

Although it is not critical to the present invention, the capture reagent also can be coated onto particles, e.g., "beads" or "microparticles". These particles can serve as the solid phase, by being retained in a column or being suspended in the mixture of soluble reagents and test sample, or the particles themselves can be retained and immobilized by a solid phase base material. By "retained and immobilized" is meant that the particles, once on the solid phase material, are not capable of substantial movement to positions elsewhere within the material. The particles can be selected by one skilled in the art from any suitable type of particulate material composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the solid phase base material being used.

"Ancillary specific binding member" is used to refer to any member of a specific binding pair which is used in the assay in addition to the specific binding members of the capture reagent and the indicator reagent. One or more ancillary specific binding members can be used in an assay.

The following describes procedures and examples of preferred embodiments of the present invention and is intended to be descriptive but not limitative of the invention.

Methods

The sample population for a PLA2 activity fluorometric assay according to the invention comprised twenty diagnosed paranoid schizophrenic patients (9 men, 11 women; mean age±SD 32±12 years), twenty one healthy controls (10 men, 11 women, mean age 31±7 years), and six diagnosed nonschizophrenic psychiatric patients (all women; mean age 37±11 years). Schizophrenic patients were diagnosed according to the Research Diagnostic Criteria (RDC), and their psychopathological state was evaluated by means of the Brief Psychiatric Rating Scale (BPRS). The mean duration of the disease was 6±8 years, and the patients were drug-free for at least one week. Eight patients were first-onset schizophrenics, who had never received neuroleptics prior to inclusion in this study. The effect of neuroleptic treatment on PLA2 was investigated in thirteen patients in whom the enzyme activity was determined before and after three weeks (mean 24±4 days) on haloperidol treatment (mean dose 14±9 mg/day). The nonschizophrenic psychiatric patients had the following RDC diagnoses: three endogenous depression, two anxiety disorder, and one unspecified functional psychosis.

The assays were performed according to the procedure of Thuren et al, as described in "Fluorometric assay for phospholipase A2 in serum", *Clinical Chemistry* 31:714-717 (1985). The detection limit of the assay was six picomoles/minute/milliliter. The interassay and intraassay coefficients of variation were 5.1% and 4.2%, respectively. Nonparametric tests were used for the statistical evaluation of the data (Mann-Whitney U-test, Wilcoxon matched pairs, and Spearman correlations, all two-tailed.)

EXAMPLE 1: PREPARATION OF SUBSTRATE

For 40 assays, evaporate 225 nmol (800 μL) of C28-O-PHPM (KSV-Chemicals OY, SF-00380 Helsinki, Finland) in a toluene/ethanol (1/1, by volume) stock solution, as provided by the manufacturer, under a gentle stream of nitrogen. Then dissolve the residue in ethanol (800 μL). Rapidly add this solution in eight successive injections with a 100 μL microsyringe (Hamilton Co., Reno, Nev.) into a test tube containing Tris buffer (5.6 mL, 20 mmol/L, pH 7.4). Keep the C28-O-PHPM solution on ice and use within four hours. Stored at −20° C., the stock solution is stable for at least six months and the ethanolic solution for at least a month.

EXAMPLE 2: ASSAY PROCEDURE

Introduce the substrate-Tris buffer solution (160 μL) of Example 1 into a glass test tube, and start the reaction by adding the serum sample (40 μL). Stir the contents of the tube thoroughly and incubate for thirty minutes at 37° C. in a water bath. Stop the enzyme reaction by adding a mixture of chloroform/methanol/heptane (1.3 mL; 1.25/1.41/1.00, by volume), and vortex-mix the solution. Then add borate-potassium carbonate buffer (300 μL, 0.14 mol/L each, pH 10.5), and thoroughly mix the solution. To separate the two phases, centrifuge the tubes for ten minutes at about 2000× g. Pipet 0.5 mL of the aqueous (upper) phase into a test tube containing methanol (2.0 mL), mix thoroughly, and transfer all of this mixture into a magnetically stirred four-window quartz cuvette.

Adjust the fluorometer settings for background correction to zero emission with the upper phase from an assay tube which is processed as a standard assay but with distilled water in place of the serum sample. For calibration, terminate two assays immediately after adding 40 μL of normal human serum. Adjust the fluorometer sensitivity settings to give a reading of 20 when the cuvette contains 200 pmol of (pyren-1-yl)hexanoic acid in 2.0 mL of methanol mixed with 0.5 mL of the upper phase from a serum-containing tube (total volume 2.5 mL).

Set fluorescence excitation at 343 nm and measure emission at 400 nm. As a control, include in every assay a series of normal serum samples containing a known concentration (20–100 μg/L) of added porcine PLA2. PLA2 activity is expressed as picomoles of free (pyren-1-yl)hexanoic acid produced per minute per milliliter of serum.

EXAMPLE 3: ASSAY PROCEDURE FOR THE SAMPLE POPULATION

The assays for the 47 patients and controls in the sample were prepared and performed as described in Examples 1 and 2 above.

Results: Baseline Comparisons (Schizophrenics versus Controls)

Drug-free schizophrenic patients had significantly higher plasma PLA2 activity than healthy controls ($p<0.001$), and higher plasma PLA2 activity than nonschizophrenic psychiatric controls. The assay results are illustrated in Table 1. Fourteen of the 20 schizophrenics (70%) had plasma PLA2 activity higher than the highest value found in healthy controls. Seven of the eight first-onset schizophrenics were within the highest values as shown in FIG. 1. No influence of sex or age on the enzyme activity was found.

TABLE 1

Phospholipase-A2 Activity (in pmol/min/ml) in EDTA-Plasma from Schizophrenics, Healthy Controls, and Nonschizophrenic Psychiatric Patients (mean ± SD)

|  | Schizophrenics (n = 20) | Healthy Controls (n = 21) | Nonschizophrenic Psychiatric Patients (n = 6) |
| --- | --- | --- | --- |
| Total | 42 ± 27[a] | 17 ± 6 | 22 ± 6 |
| Men | 39 ± 27[a] | 18 ± 6 | — |
| Women | 44 ± 29[a] | 16 ± 6 | 22 ± 6 |

[a] $p < 0.001$

No correlations were found between baseline PLA2 activity and the psychopathological scores from the BPRS. Plasma PLA2 activity correlated negatively with the duration of the disease ($r_r = -0.40$, $p<0.05$) and with the total duration of psychiatric hospital treatments during the course of the illness ($r_s = -0.37$, $p<0.05$).

Effects of Neuroleptic Treatment

Figure 2:
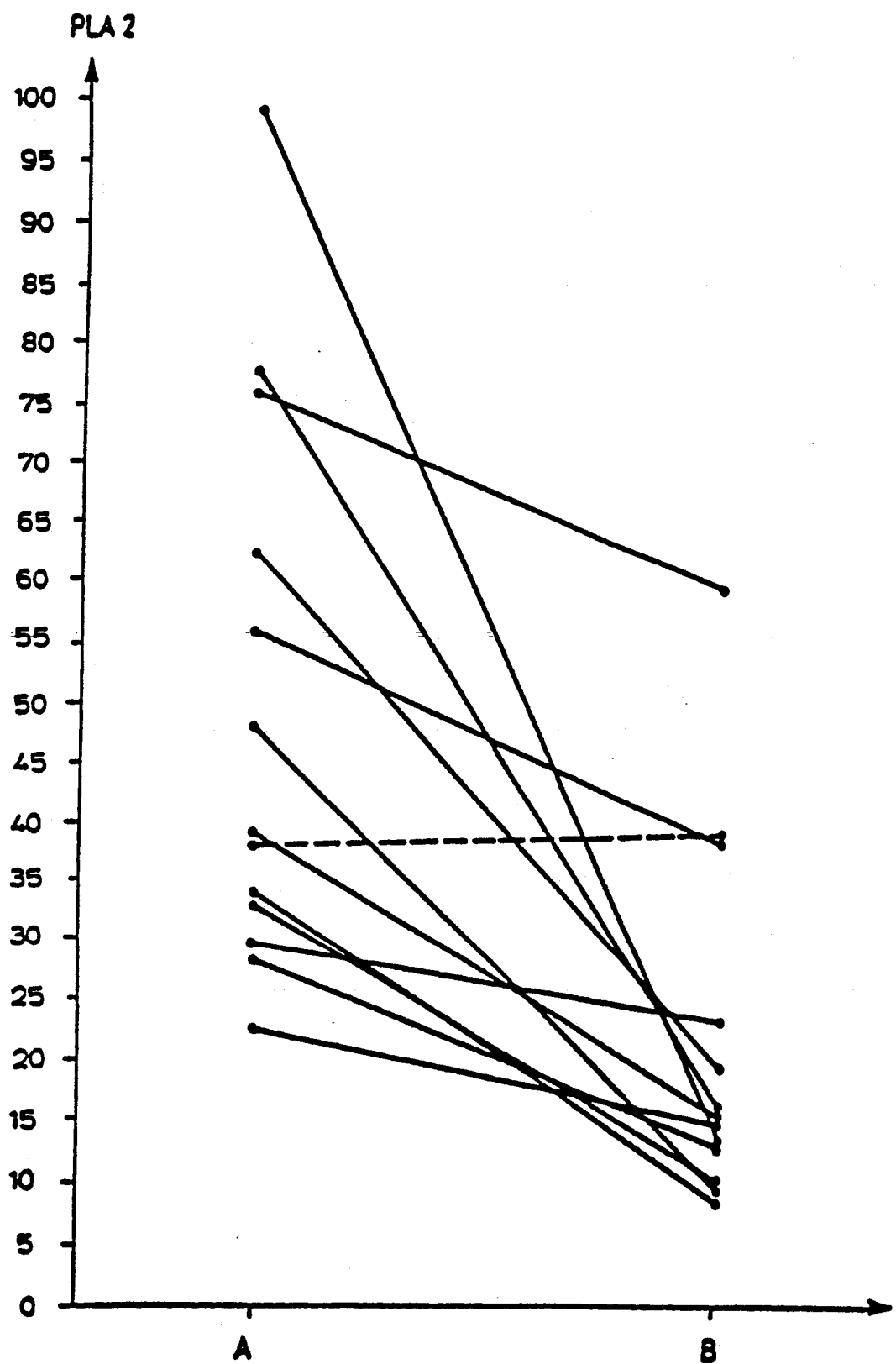
FIG. 2 is a graphical representation showing phospholipase-A2 activity levels in thirteen schizophrenics before (A) and after (B) three weeks of haloperidol therapy. (See Results: Effects of Neuroleptic Treatment.)

Haloperidol treatment was found to have reduced the plasma PLA2 activity in all but one patient (before treatment 49±23, after treatment 21±15 pmol/min/ml; $p<0.001$) (FIG. 2.). There was a significant reduction in all BPRS scores after the drug treatment (total BPRS score before treatment 63±9, after treatment 30±12; $p<0.001$). However, the psychopathological improvement did not correlate with the reduction in the enzyme activity.

Based upon this investigation, it was found that the levels of PLA2 activity in plasma could differentiate 70% of the schizophrenic patients from the healthy controls in the sample population. It is unlikely that the increased enzyme activity in schizophrenics is secondary to some psychopathological features (such as psychomotor activation and anxiety), as no correlations were found between PLA2 and activity and BPRS scores.

The possibility that increased plasma PLA2 in schizophrenics reflects a late effect of prior neuroleptic treatment could be obviated by the findings that neuroleptics tended to reduce the enzyme activity and that all but one first-onset never-treated schizophrenic were also within the highest values. Additionally, the baseline enzyme activity correlated negatively with the duration of the disease and with the total duration of psychiatric hospital treatment prior to the study; these two interdependent variables might reflect the total amount of neuroleptic intake during the course of the disease. Thus, it seems reasonable to assume that prior neuroleptic intake could at best reduce the magnitude of the difference between schizophrenics and controls.

The observed effect of haloperidol on PLA2 activity is in agreement with the results of in vitro and animal experiments in which other neuroleptic drugs (chlorpromazine and trifluoperazine) were found to inhibit the enzyme activity.

There are two possibilities for consideration regarding the difference in plasma PLA2 activity between schizophrenic patients and the healthy controls. First, the finding of increased plasma PLA2 activity in schizophrenics may be restricted to the pancreatic form of the enzyme. The cleavage of phospholipids by pancreatic PLA2 not only generates free fatty acids, but also highly toxic compounds, such as lysophosphatidylcholine. One can speculate as to whether or not abnormally high levels of toxic compounds produced by increased PLA2 activity cross from the blood to the brain and disrupt normal function and/or plasticity in schizophrenia. Such an assumption would follow the model of phenylketonuria, a neuropsychiatric disorder probably caused by an enzymatic dysfunction in the liver.

A second possibility is that the findings reflect an increased activity of the intracellular PLA2. This is supported by reports of an immunochemical relatedness between secretory and intracellular PLA2; increased intracellular PLA2 activity would accord with the finding of reduced phosphatidylcholine content in erythrocyte ghost membranes from schizophrenic patients. PLA2 is known to be concentrated in neuronal membranes, where it controls the phospholipid turnover. The most likely reason for phospholipid turnover appears to be that it modulates and/or sustains membrane integrity and membrane function. The in vitro activation of intracellular PLA2 causes changes in the physicochemical characteristics of synaptosomal membranes, leading to an increased release of neurotransmitters through exocytosis. The possible participation of such mechanisms underlying disordered brain function and plasticity in schizophrenia may be elucidated by further studies in this area.

The concepts of the present invention are applicable to various types of direct enzyme assays as well as binding assays. It will be appreciated, however, that one skilled in the art can conceive of many other types of assays to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method for the diagnosis of schizophrenia, comprising:
   (a) combining a test sample with a substrate capable of detecting phospholipase-A2 in the test sample;
   (b) obtaining a measurement of the amount of said phospholipase-A2 in the test sample;
   (c) comparing the measured amount to phospholipase-A2 values found in nonschizophrenic controls; and
   (d) diagnosing schizophrenia if said test sample measurement is increased relative to phospholipase-A2 values found in nonschizophrenic controls.

2. The method according to claim 1, wherein said substrate comprises a chromogenic substrate specific for said phospholipase-A2.

3. The method according to claim 1, wherein said substrate comprises a fluorogenic substrate specific for said phospholipase-A2.

4. A process for the diagnosis of schizophrenia, comprising:
   (a) providing
      (1) a capture reagent, comprising a first binding member specific for phospholipase-A2, and
      (2) an indicator reagent, comprising a second binding member specific for said phospholipase-A2 conjugated to a label capable of producing a detectable signal;
   (b) contacting a test sample with said capture reagent, whereby said capture reagent becomes bound to said phospholipase-A2 in the sample, thereby forming a capture reagent/phospholipase-A2 complex;
   (c) contacting said capture reagent/phospholipase-A2 complex with said indicator reagent, whereby said indicator reagent becomes bound to said phospholipase-A2, thereby forming a capture reagent/phospholipase-A2/indicator reagent sandwich complex;
   (d) detecting said label associated with said sandwich complex or unbound indicator reagent as an indication of the presence or amount of phospholipase-A2 in the sample;
   (e) comparing the presence or amount of the phospholipase-A2 to phospholipase-A2 values found in nonschizophrenic controls; and
   (f) diagnosing schizophrenia if said test sample measurement is increased relative to phospholipase-A2 values found in nonschizophrenic controls.

5. The process according to claim 4, wherein said first and second specific binding members are selected from the group consisting of effector molecules, receptor molecules, enzyme cofactors, enzyme inhibitors, antibodies and antibody fragments.

6. The process according to claim 5 wherein said antibody is a monoclonal antibody, polyclonal antibody or recombinant antibody.

7. The process according to claim 4, wherein said capture reagent is retained by an insoluble solid phase material.

8. The process according to claim 7, wherein said solid phase material is a porous material.

9. The process according to claim 8, wherein a plurality of microparticles, coated with said capture reagent, are retained by said porous material.

10. The process according to claim 7, wherein said solid phase material comprises a plurality of microparticles.

11. The process according to claim 4, wherein said capture reagent and said indicator reagent are simultaneously contacted with the sample.

12. A process for the diagnosis of schizophrenia, comprising:
   (a) providing
      (1) a capture reagent, comprising a first binding member specific for phospholipase-A2, and
      (2) an indicator reagent, comprising a second binding member specific for the first binding member conjugated to a label capable of producing a detectable signal;
   (b) contacting a test sample with said capture reagent and said indicator reagent, whereby said phospholipase-A2 in the sample competes with said indicator reagent to bind to said capture reagent, thereby forming capture reagent/phospholipase-A2 complex and capture reagent/indicator reagent complex;
   (c) detecting said label associated with said capture reagent or unbound indicator reagent as an indication of the presence or amount of said phospholipase-A2 in the sample;
   (d) comparing the presence or amount of said phospholipase-A2 to phospholipase-A2 values found in nonschizophrenic controls; and
   (e) diagnosing schizophrenia if said test sample measurement is increased relative to phospholipase-A2 values found in nonschizophrenic controls.

13. The process according to claim 12, wherein said first and second specific binding members are selected from the group consisting of effector molecules, receptor molecules, enzyme cofactors, enzyme inhibitors, antibodies and antibody fragments.

14. The process according to claim 13 wherein said antibody is a monoclonal antibody, polyclonal antibody, or recombinant antibody.

15. The process according to claim 12, wherein said capture reagent is retained by an insoluble solid phase material.

16. The process according to claim 15, wherein said solid phase material is a porous material.

17. The process according to claim 16, wherein a plurality of microparticles, coated with said capture reagent, are retained by said porous material.

18. The process according to claim 15, wherein said solid phase material comprises a plurality of microparticles.

19. The process according to claim 12, wherein said capture reagent and said indicator reagent are sequentially contacted with the sample.

20. The process according to claim 19, wherein said first and second specific binding members are selected from the group consisting of complementary nucleic acid sequences, effector molecules, receptor molecules, enzyme cofactors, enzyme inhibitors, antibodies and antibody fragments.

21. A method for the diagnosis of schizophrenia, comprising:
   (a) combining a test sample with at least one specific binding member capable of binding to phospholipase-A2 thereby forming a detectable complex;
   (b) detecting and measuring said complex, thereby obtaining a measurement of the amount of said phospholipase-A2 in the test sample;

(c) comparing the measurement in step (b) to phospholipase-A2 values found in nonschizophrenic controls; and (d) diagnosing schizophrenia if said test sample measurement is increased relative to phospholipase-A2 values found in nonschizophrenic controls.

22. The method according to claim 21, wherein said specific binding member is selected from the group consisting of complementary nucleic acid sequences, effector molecules, receptor molecules, enzyme cofactors, enzyme inhibitors, antibodies and antibody fragments.

23. The method according to claim 22, wherein said specific binding member is an antibody.

24. The method according to claim 23, wherein said antibody is selected from the group consisting of a monoclonal antibody, a polyclonal antibody, an or recombinant antibody.

25. A process for the diagnosis of schizophrenia, comprising:

(a) providing
  (1) a capture reagent, comprising a first binding member specific for phospholipase-A2,
  (2) an indicator reagent, comprising a second binding member specific for said phospholipase-A2 conjugated to a label capable of producing a detectable signal, and
  (3) an ancillary specific binding member specific for said capture reagent and retained upon a solid phase;

(b) contacting a test sample with said capture reagent, whereby said capture reagent becomes bound to said phospholipase-A2 in the sample, thereby forming a capture reagent/phospholipase-A2 complex;

(c) contacting said capture reagent/phospholipase-A2 complex with said indicator reagent, whereby said indicator reagent becomes bound to said phospholipase-A2, thereby forming a capture reagent/phospholipase-A2/indicator reagent sandwich complex;

(d) contacting said sandwich complex with said ancillary specific binding member, thereby forming a solid phase bound sandwich complex and allowing the separation of said bound sandwich complex from unreacted test sample and reagents;

(e) detecting said label associated with said bound sandwich complex or unbound indicator reagent as an indication of the presence or amount of phospholipase-A2 in the sample;

(f) comparing the presence or amount of the phospholipase-A2 to phospholipase-A2 values found in nonschizophrenic controls; and (g) diagnosing schizophrenia if said test sample measurement is increased relative to phospholipase-A2 values found in nonschizophrenic controls.

26. A process for the diagnosis of schizophrenia, comprising:

(a) providing
  (1) a capture reagent, comprising a first binding member specific for phospholipase-A2,
  (2) an indicator reagent, comprising a second binding member specific for said phospholipase-A2, and
  (3) an ancillary specific binding member, specific for said indicator reagent, conjugated to a label capable of producing a detectable signal;

(b) contacting a test sample with said capture reagent, whereby said capture reagent becomes bound to said phospholipase-A2 in the sample, thereby forming a capture reagent/phospholipase-A2 complex;

(c) contacting said capture reagent/phospholipase-A2 complex with said indicator reagent, whereby said indicator reagent becomes bound to said phospholipase-A2, thereby forming a capture reagent/phospholipase-A2/indicator reagent sandwich complex;

(d) contacting said sandwich complex with said ancillary specific binding member, thereby forming a labeled sandwich complex;

(e) detecting said label associated with said labeled sandwich complex or unbound ancillary specific binding member as an indication of the presence or amount of phospholipase-A2 in the sample;

(f) comparing the presence or amount of the phospholipase-A2 to phospholipase-A2 values found in nonschizophrenic controls; and (g) diagnosing schizophrenia if said test sample measurement is increased relative to phospholipase-A2 values found in nonschizophrenic controls.

27. A process for the diagnosis of schizophrenia, comprising:

(a) providing
  (1) a capture reagent, comprising a first binding member specific for phospholipase-A2,
  (2) an indicator reagent, comprising a second binding member specific for the first binding member conjugated to a label capable of producing a detectable signal, and
  (3) an ancillary specific binding member specific for said capture reagent and retained upon a solid phase;

(b) contacting a test sample with said capture reagent and said indicator reagent, whereby said phospholipase-A2 in the sample competes with said indicator reagent to bind to said capture reagent, thereby forming capture reagent/phospholipase-A2 complex and capture reagent/indicator reagent complex;

(c) contacting said complexes with said ancillary specific binding member, thereby forming solid phase bound complexes and allowing the separation of said bound complexes from unreacted test sample and reagents;

(d) detecting said label associated with said bound complexes or unbound indicator reagent as an indication of the presence or amount of said phospholipase-A2 in the sample;

(e) comparing the presence or amount of said phospholipase-A2 to phospholipase-A2 values found in nonschizophrenic controls; and (f) diagnosing schizophrenia if said test sample measurement is increased relative to phospholipase-A2 values found in nonschizophrenic controls.

28. A process for the diagnosis of schizophrenia, comprising:

(a) providing
  (1) a capture reagent, comprising a first binding member specific for phospholipase-A2,
  (2) an indicator reagent, comprising a second binding member specific for the first binding member, and
  (3) an ancillary specific binding member specific for said indicator reagent and conjugated to a label capable of producing a detectable signal;

(b) contacting a test sample with said capture reagent and said indicator reagent, whereby said phospholipase-A2 in the sample competes with said indicator reagent to bind to said capture reagent, thereby forming capture reagent/phospholipase-A2 complex and capture reagent/indicator reagent complex;

(c) contacting said complexes with said ancillary specific binding member, thereby forming a labeled capture reagent/indicator reagent/ancillary specific binding member complex;

(d) detecting said labeled complex or unbound indicator reagent as an indication of the presence or amount of said phospholipase-A2 in the sample;

(e) comparing the presence or amount of said phospholipase-A2 to phospholipase-A2 values found in nonschizophrenic controls; and (f) diagnosing schizophrenia if said test sample measurement is increased relative to phospholipase-A2 values found in nonschizophrenic controls.

* * * * *